United States Patent [19]
Oude Alink et al.

[11] 4,104,249
[45] Aug. 1, 1978

[54] HEXAHYDROPYRIMIDINES AS ANTI-OXIDANTS IN NATURAL AND SYNTHETIC RUBBERS

[75] Inventors: Bernardus A. Oude Alink, St. Louis; Neil E. S. Thompson, Creve Coeur, both of Mo.

[73] Assignee: Petrolite Corporation, St. Louis, Mo.

[21] Appl. No.: 691,530

[22] Filed: Jun. 1, 1976

[51] Int. Cl.$^2$ .................. C08K 5/34; C07D 239/02; C07D 239/06; C07D 239/70
[52] U.S. Cl. .................. 260/45.8 N; 260/814; 544/231; 544/242; 544/253
[58] Field of Search ......... 260/45.8 N, 251 R, 251 A, 260/251 Q, 814

[56] References Cited

U.S. PATENT DOCUMENTS

| | | | |
|---|---|---|---|
| 2,525,855 | 10/1950 | Bergmann | 260/251 |
| 3,248,243 | 4/1966 | Hodge et al. | 260/45.8 N |
| 3,277,045 | 10/1966 | Bonvicini et al. | 260/45.8 N |
| 3,904,625 | 9/1975 | Oude Alink | 260/251 R |
| 3,943,134 | 3/1976 | Kajiyama et al. | 260/251 R |

*Primary Examiner*—H.S. Cockeram
*Attorney, Agent, or Firm*—Sidney B. Ring; Hyman F. Glass

[57] ABSTRACT

This invention relates to the use of hexahydropyrimidines (HHP) as anti-oxidants for elastic materials such as rubber.

The preferred hexahydropyrimidines contain at least one cycloalkylene or substituted cycloalkylene group and most preferably three cycloalkylene groups as illustrated by 2,2,4,4-dipentamethylene-5,6-tetramethylene hexahydropyrimidine.

14 Claims, No Drawings

HEXAHYDROPYRIMIDINES AS ANTI-OXIDANTS IN NATURAL AND SYNTHETIC RUBBERS

In Ser. No. 292,494 filed on Sep. 27, 1972 there is described and claimed substituted 2, 3, 4, 5-tetrahydropyrimidines (THP)

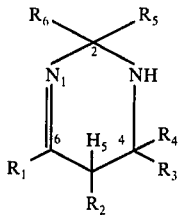

which are prepared by the following reactions:

(1) The reaction of a carbonyl compound (ketone or aldehyde) with $NH_3$ (or $NH_4OH$) and a sulfur-containing catalyst.

(2) The reaction of an $\alpha,\beta$-unsaturated ketone and a carbonyl compound and $NH_3$ (or $NH_4OH$) without a catalyst.

(3) Reaction of an $\alpha,\beta$-unsaturated ketone, a 1-amino-alcohol and $NH_3$ (or $NH_4OH$) without a catalyst.

In the above formula, $R_1$, $R_2$, $R_3$, $R_4$, $R_5$ and $R_6$, which may be the same or different, are hydrogen or substituted group such as alkyl, aryl, cycloalkyl, alkaryl, aralkyl, heterocyclic, substituted derivatives thereof, etc. In addition R groups may be joined in a cyclic configuration which makes the THP structure a part of the substituted group.

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, escosyl, docosyl, etc. for example having about 1–25 or more carbons such as from about 1–18 carbons, but preferably about 1–12 carbons. The term "alkyl" also includes isomers of the straight chain where branching occurs.

Cycloalkyl includes cyclopentyl, cyclohexyl, etc. and derivatives thereof such as alkyl cyclohexyl, dialkylcyclohexyl, etc.

Aryl, alkaryl and aralkyl include phenyl, alkylphenyl, polyalkylphenyl, chlorophenyl, alkoxyphenyl, naphthyl, alkylnaphthyl, etc., benzyl, substituted benzyl, etc.

The joining of the R groups into a ring structure include those structures derived from reactants of the general formula $(CH_2)_n C = O$ such as cyclohexanone, cyclopentanone, substituted derivatives thereof such as alkyl-cyclohexanone, dialkyl-cyclohexanone.

In Ser. No. 406,544 filed Oct. 15, 1973 there is described and claimed a class of compounds which are prepared by reducing THP.

Said Ser. No. 406,544 describes and claims a unique method of preparing HHP which comprises using a formate salt such as ammonium formate. The use of ammonium formate is unique for the following reasons:

(1) In the preparation of THP from a carbonyl compound and ammonia, ammonium formate operates as a very efficient catalyst without being consumed.

(2) In the preparation of HHP from THP, ammonium formate serves as a reducing agent, yielding $CO_2$ and $NH_3$ as byproducts. It is often preferred to form ammonium formate by allowing ammonia to react with formic acid present during the initial phase of the reaction. The byproducts, produced in the process of preparing HHP from a carbonyl compound, formic acid and ammonia, are $H_2O$, $CO_2$, and $NH_3$ and are all easily removed.

The specific reaction is as follows:

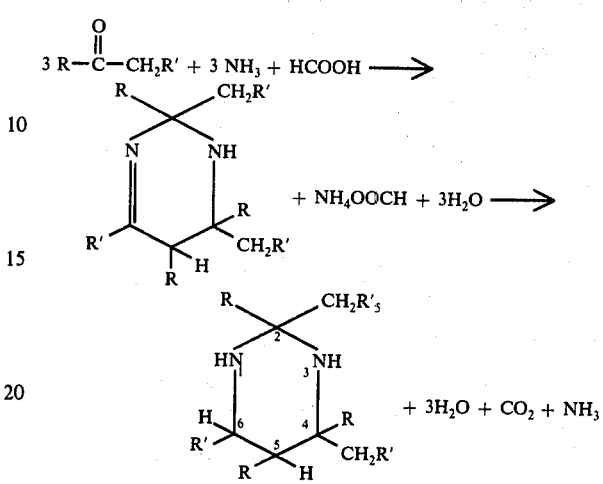

If a symmetric carbonyl compound is employed, i.e., $R = CH_2R'$ a single HHP will be produced, for example in the case of cyclohexanone, the reaction may be summarized as follows:

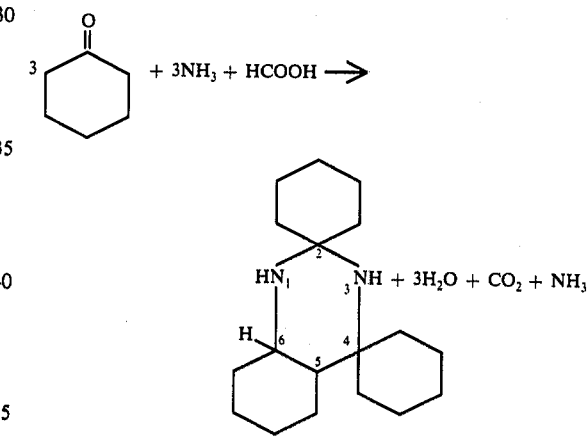

In the preferred method of Ser. No. 406,544, the carbonyl compound is reacted with ammonia in the presence of ammonium formate (or formic acid so as to form ammonium formate in situ) under pressure to keep the volatile components in the reaction mixture. The reaction is carried out at a temperature and time sufficient to produce THP, for example at a temperature of 20° – 100° C. or higher, such as from 20°–55° C. for preferably from 2–18 hrs.

In general the molar ratio of carbonyl to $NH_3$ to formic acid is at least 3 to 3 to 1 but preferably 3 to 3–4 to 1.

After completion of the formation of THP, the reaction mixture is further heated, preferably under reduced pressure to remove $H_2O$, $CO_2$ and $NH_3$ at a temperature of 40°–200° C. for 0.5 to 24 hrs. to produce HHP.

The preferred carbonyl compound is cyclohexanone. Not all carbonyl compounds can be used. For example methyl ethyl ketone (MEK) when reacted with ammonia in the presence of formic acid yields a mixture of 2,4,5,6-tetramethyl-2,4-diethyl and 2,4-dimethyl-2,4,6- triethyl-2,3,4,5-tetrahydropyrimidine which upon further reaction with ammonium formate gives a mixture of dihydropyridines, a process involving deammoniation rather than reduction of the tetrahydropyrimidine moiety. However, MEK in combination with cyclohexanone yields the HHP.

Substituted cyclohexanones can also be used. Also mixtures of cyclohexanones and other ketones or aldehydes can be used so as to yield mixtures of substituted hexahydropyrimidines.

The following examples are presented by way of illustration and not of limitation.

EXAMPLE 1

2,2,4,4-Dipentamethylene-5,6-tetramethylene hexahydropyrimidine

A mixture of 294 grams of cyclohexanone and 51 grams of 90% formic acid were placed in a pressure reactor. To the mixture was added with cooling and stirring 58.6 grams of ammonia gas over a 1/2 hour period. The mixture was stirred for 18 hours at ambient temperature. The resulting product was subjected to a vacuum (25 mm Mg) at 60° C. and the distillate 18 grams of unreacted cyclohexanone (6%) and water was discarded. The product was further heated for 3 hours at 120–125° C. The resulting product 237.6 grams (86%) was identified as 2,2,4,4-Dipentamethylene-5,6-tetramethylene hexahydropyrimidine, $b_{0.5}$ 153°–155° C.

Anal. Calc.ed for $C_{18}H_{32}N_2$; C, 78.20; H, 11.67; N, 10.14. Found; C, 77.94; H, 11.74; N, 10.08.

EXAMPLE 2

2,2,4,4-Dipentamethylene-5,6-tetramethylene hexahydropyrimidine

A mixture of 294 grams of cyclohexanone and 63 grams of ammonium formate were placed in a pressure reactor. To the mixture was added 41 grams of ammonia gas over a 1 hour period. The mixture was stirred for 18 hours at ambient temperature. The resulting heterogeneous mixture was heated under diminished pressure to 125° C. and kept at 125° C. for 3½ hours. The resulting product, 238 grams, was identical in all respects to the product described in example 1.

In a manner as described in example 1, HHP's were prepared from 2-methyl cyclohexanone, 3-methyl cyclohexanone, 4-methyl cyclohexanone, mixture of cyclohexanone and acetone; cyclohexanone and methyl ethyl ketone; cyclohexanone and cyclopentanone; cyclohexanone and propionaldehyde; cyclohexanone and cycloheptanone.

They are summarized as follows.

| | CARBONYL EMPLOYED | | |
|---|---|---|---|
| Ex | A | B | Molar Ratio A/B |
| 3 | 2-methyl cyclohexanone | — | |
| 4 | 3-methyl cyclohexanone | — | |
| 5 | 4-methyl cyclohexanone | — | |
| 6 | cyclohexanone | acetone | 2 |
| 7 | cyclohexanone | methyl ethyl ketone | 2 |
| 8 | cyclohexanone | cyclopentanone | 1 |
| 9 | cyclohexanone | propionaldehyde | 2 |
| 10 | cyclohexanone | cycloheptanone | 1 |

The products of the above reactions where HHP are prepared are summarized in the following table:

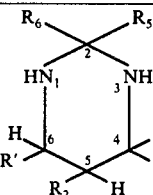

| RING Position | 6 | 5 | 4 | 4 | 2 | 2 |
|---|---|---|---|---|---|---|
| Ex. | Subst. Group $R_1$ | $R_2$ | $R_3$ | $R_4$ | $R_5$ | $R_6$ |
| 1 | —(CH$_2$)$_4$— | | —(CH$_2$)$_5$— | | —(CH$_2$)$_5$— | |
| 2 | —(CH$_2$)$_4$— | | —(CH$_2$)$_5$— | | —(CH$_2$)$_5$— | |
| 3 | —CH—(CH$_2$)$_3$— \| CH$_3$ | | —CH—(CH$_2$)$_4$— \| CH$_3$ | | —CH—(CH$_2$)$_4$— \| CH$_3$ | |
| 4 | —CH$_2$—CH—(CH$_2$)$_2$— \| CH$_3$ | | —CH$_2$—CH—(CH$_2$)$_3$— \| CH$_3$ | | —CH$_2$—CH—(CH$_2$)$_3$— \| CH$_3$ | |
| 5 | —(CH$_2$)$_2$—CH—CH$_2$— \| CH$_3$ | | —(CH$_2$)$_2$—CH—(CH$_2$)$_2$— \| CH$_3$ | | —(CH$_2$)$_2$—CH—(CH$_2$)$_2$— \| CH$_3$ | |
| 6 | Mixtures of Products | CH$_3$ or —(CH$_2$)$_4$— | H | CH$_3$ or —(CH$_2$)$_5$— | CH$_3$ | CH$_3$ or —(CH$_2$)$_5$— | CH$_3$ |
| 7 | Mixture of Products | CH$_3$ or C$_2$H$_5$ or —(CH$_2$)$_4$— | CH$_3$ H | CH$_3$ or —(CH$_2$)$_5$— | C$_2$H$_5$ | CH$_3$ or —(CH$_2$)$_5$— | C$_2$H$_5$ |
| 8 | Mixtures of Products | —(CH$_2$)$_4$— or —(CH$_2$)$_5$— | | —(CH$_2$)$_5$— or —(CH$_2$)$_5$— | | —(CH$_2$)$_5$— or —(CH$_2$)$_5$— | |
| 9 | Mixtures of Products | —(CH$_2$)$_4$— or —(CH$_2$)$_5$— | | —(CH$_2$)$_5$— or —(CH$_2$)$_4$— | | —(CH$_2$)$_4$— —(CH$_2$)$_5$— | |
| 10 | Mixtures Products | or H —(CH$_2$)$_4$— or —(CH$_2$)$_5$— | C$_2$H$_5$ | or H —(CH$_2$)$_5$— or —(CH$_2$)$_6$— | C$_3$H$_7$ | or H —(CH$_2$)$_5$— —(CH$_2$)$_6$— | C$_3$H$_7$ |

In addition THP can be prepared by the methods described in said Ser. No. 292,494 and reduced to HHP by any conventional reducing technique such as for example with sodium-ethanol, sodiumborohydride, LiAlH$_4$, sodium bisulfite, magnesium-methanol, a hydrogenation catalyst such as platinum, palladium, cobalt, nickel, etc.

EXAMPLE A

To a mixture of 294 grams of cyclohexanone and 5 grams of ammonium chloride placed in a pressure reactor was added over a ¾ hour period 38.8 grams of ammonia gas. After the addition was completed, the mixture was stirred for 5 hours at ambient temperature. The product was taken up in toluene and the aqueous phase which separated was discarded. The toluene solution was evaporated under diminished pressure to yield 268 grams of 2,2,4,4-dipentamethylene-5,6-tetramethylene-2,3,4,5-tetrahydropyrimidine.

A sample of 27.4 grams of 2,2,4,4-dipentamethylene-5,6-tetramethylene-2,3,4,5-tetrahydropyrimidine was dissolved in 50 grams of ethanol. To the ethanolic solution was added 6.9 grams of sodium metal at such a rate that a temperature of 70°–80° C. was maintained. After the addition was completed, the mixture was heated for 1 hour at 85°–95° C. The mixture was allowed to cool to ambient temperature and water was added. The organic layer which separated was taken up in toluene. The toluene solution after washing with water was evaporated under diminished pressure to yield 22.1 grams of 2,2,4,4-dipentamethylene-5,6-tetramethylene hexahydropyrimidine identical to the product prepared in example 1.

EXAMPLE B

To a sample of 27.4 grams of 2,2,4,4-dipentamethylene-5,6-tetramethylene-2,3,4,5-tetrahydropyrimidine dissolved in 95 grams of ethanol was added 2 grams of 5% platinum charcoal catalyst. The mixture was hydrogenated in a hydrogenator for 7 hours at an initial pressure of 40 psi of hydrogen. The catalyst was filtered off and the ethanolic solution evaporated under diminished pressure to yield 26 grams of 2,2,4,4-dipentamethylene-5,6-tetramethylene hexahydropyrimidine identical to the product described in example A.

EXAMPLE C

A sample of 81.2 grams of 2,2,4,4-dipentamethylene-5,6-tetramethylene-2,3,4,5-tetrahydropyrimidine and 32.3 grams of triethylamine were heated to 85° C. Over a 2 hour period was added 23 grams of 90% formic acid while a reaction temperature of 85° C. was maintained. After the addition was completed, the mixture was kept at 85° C. for 16 hours. Water was added and the organic layer isolated and evaporated under diminished pressure to yield 60.3 grams of 2,2,4,4-dipentamethylene-5,6-tetramethylene hexahydropyrimidine.

The compositions of this invention are useful as fuel additives, corrosion inhibitors, biocides, i.e., bacteriocides, algecides, etc.

We have now discovered that the hexahydropyrimidines described in Ser. No. 406,544 are also rubber stabilizers and/or anti-oxidants.

The preferred hexahydropyrimidines of this invention contain at least one cycloalkylene or substituted cycloalkylene and most preferably three cycloalkylene or substituted cycloalkylene groups preferably those having a ring of 5–7 carbons and most preferably 6 carbons, i.e., cyclohexyl.

These are ideally presented by the following formulae

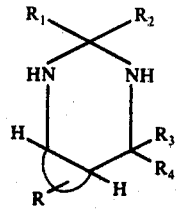

such as

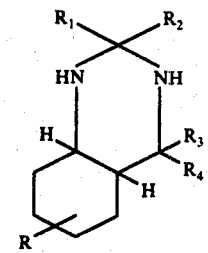

preferably

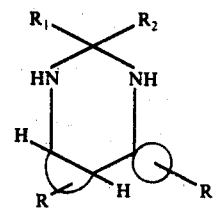

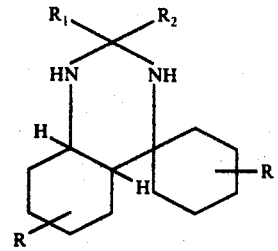

most preferably

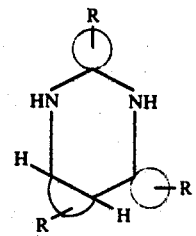

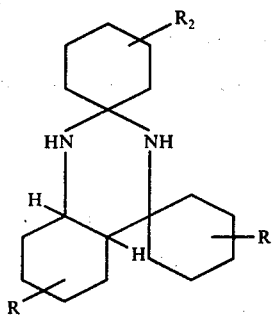

where the R's are hydrogen, alkyl, cycloalkyl, alkaryl, aralkyl, heterocyclic, and substituted derivatives thereof and the circles represent cycloalkylene structures.

The hexahydropyrimidines (HHP) of this invention are employed in amounts sufficient to act as stabilizers and/or anti-oxidants. Suitable amounts will vary with the particular HHP and/or the particular rubber. They may be incorporated in minor amounts, for example from about 0.25 to about 5 or more parts of HHP based on 100 parts by weight of rubber such as from 0.5 to 4 parts for example from 1 to 3 parts, but preferably from about 1.5-2 parts.

HHP is incorporated into a sufficient quantity of SBR latex to provide about 1-2 parts of HHP per 100 parts of synthetic rubber to yield to the improved rubbers of the present invention.

The following is an example of a rubber formulation, prepared with the products of this invention employed as anti-oxidants.

The formula of the masterbatch is as follows. In all other examples, the same master batch is employed except that the compound tested is added as shown in Table I.

| Masterbatch | |
|---|---|
| SBR 1502 (styrene-Butadiene Latex) | 100.0 gm. |
| Stearic Acid | 1.0 |
| Zinc Oxide | 3.0 |
| Statex R N-330 | 50.0 |
| Sulfur | 2.0 |
| Santocure | 1.2 |
| | 157.2 gm. |

TABLE I

| Compound | | A | B | C |
|---|---|---|---|---|
| A | Masterbatch (without additive) | 157.2 | 157.2 | 157.2 |
| B | with 2,2,4,4-dipentamethylene-5,6-tetramethylene hexahydropyrimidine | — | 2.0 | — |
| C | with Agerite Resin D | — | — | 2.0 |

TABLE II

| Compound | Total Mill Time | Incorporation Time | Mill Temperature |
|---|---|---|---|
| A | 7 minutes | — | 150° F |
| B | 7 minutes | 4¼ minutes | 150° F |
| C | 7 minutes | 2¼ minutes | 150° F |

Comments

All compounds incorporated easily. They did not make the compound tacky or hard to handle. They did not leave a slick surface on the mill rolls of rubber. There was no irritation to the skin or eyes.

Tensile slabs were prepared and cured 14 minutes at 320° F. The properties of the slabs are listed below.

TABLE III

| | A | B | C |
|---|---|---|---|
| A. Unaged Physicals-ASTM D412, ASTM D2240 | | | |
| Elongation, % | 290 | 410 | 370 |
| 200% Modulus, p.s.i. | 1880 | 1280 | 1520 |
| Tensile Strength, p.s.i. | 3390 | 3770 | 3740 |
| Hardness, Shore A | 68 | 66 | 68 |
| B. Air Aged-7 days at 158° F. ASTM D573 | | | |
| Elongation, % | 220 | 370 | 250 |
| % Change | −24.1% | −9.8% | −32.4% |
| 200% Modulus, p.s.i. | 2960 | 1780 | 2530 |
| % Change | +57.4% | +39.1% | +66.4% |
| Tensile Strength, p.s.i. | 3370 | 3950 | 3880 |
| % Change | −.6% | +4.8% | +3.7% |
| Hardness, Shore A | 78 | 74 | 77 |
| Points Change | +10 | +8 | +9 |
| C. Air Aged-72 hours at 212° F. ASTM D573 | | | |
| Elongation, % | 200 | 320 | 220 |
| % Change | −31.0% | −22.0% | −40.5% |
| 200% Modulus, p.s.i. | — | 1880 | 2810 |
| % Change | — | +47.0% | +84.9% |
| Tensile Strength, p.s.i. | 2970 | 3650 | 3780 |
| % Change | −12.4% | −3.2% | −1.1% |
| Hardness, Shore | 78 | 74 | 77 |
| Points Change | +10 | +8 | +9 |

In addition, the compositions of this invention are non-staining.

A disadvantage of many anti-oxidants is staining and discoloration - i.e., a darkening in color of the vulcanized rubber in which they are used. This effect is particularly noticeable upon exposure to light. Articles originally of the one color may take on various shades according to the amount of exposure. Staining is masked in black articles, so the most potent anti-oxidants may be used here, even though they are of the staining type. In many cases, for example in rubber flooring, light colors with good aging properties are essential. To meet such cases non-staining anti-oxidants have been developed. Until recently these were of low efficiency and only relatively non-staining. Within the last few years however, intensive research by makers of antioxidants has led to the introduction of new types, which combine efficiency and the absence of staining.

The following tests illustrate the non-discoloring and non-staining properties of the products of this invention.

| Contact and Migration Staining |
|---|

ASTM D925, Methods A and B on white acrylic enamel, 48 hours at 140° F. Specimens exposed 10" from R. S. bulb.

| | Control | Compound B* | Agerite Resin D |
|---|---|---|---|
| Staining after 24 hours exposure | no migration | no migration | no migration |
| Staining after 48 hours exposure | no migration no contact | no migration no contact | some migration no contact |
| Comment: | Compound B is non-staining and non-discoloring which makes it better than Agerite Resin D, a standard for the industry. | | |

*Compound B is 2,2,4,4-dipentamethylene-5,6-tetramethylenehexahydropyrimidine.

Discussion

Compound B does not detrimentally affect the tensile strength of the unaged compounds. Compound B and Agerite Resin D slightly retard cure. Compound B is an excellent anti-oxidant. Its aged and unaged tensile strength compares favorably with Agerite Resin D, while offering some advantages. For example, its lower modulus and higher elongation in the unaged and aged state could be a very useful property. In addition, Compound B is non-staining.

HHP's can be added not only to aqueous emulsions or dispersions of 1,3-butadiene-styrene copolymer rubber (SBR), but also to stabilize emulsions or dispersions of conjugated diene polymerizate rubbers generally, which would also include such as 1,3-butadiene-acrylonitrile, 1,3-butadiene-vinyltoluene, 1,3-butadiene-methyl methacrylate, 1,3-butadiene-methyl acrylate, 1,3-butadienevinyl pyridine, polybutadiene, and polyisoprene.

These anti-oxidants can also be employed in natural rubbers.

HHP's of this invention may be used with or without other preservatives or with fillers, accelerators, vulcanizing agents, or compounding ingredients of any desired sort known to the art. The components of the rubber compositions may be used in various ratios and it is not intended to limit the invention to the amounts of ingredients indicated in the examples given.

The invention may be used in the manufacture of tubes, hose, wire insulation, boots, shoes, surgical instruments, drug sundries, dipped synthetic rubber articles, vehicle tires, coating compositions, etc.

It is evident to those skilled in the art that various modifications can be made in the invention herein described without departing from the spirit of the invention and such modifications are considered as part of this invention.

We claim:

1. A rubber composition containing an antioxidant amount of a hexahydropyrimidine of the formula

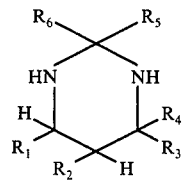

where the R's are hydrogen, alkyl, aryl, cycloalkyl, aralkyl, alkaryl or heterocyclic, and where $R_1$ and $R_2$ may be joined to form a cycloalkyl group, $R_3$ and $R_4$ may be joined to form a cycloalkyl group and $R_5$ and $R_6$ may be joined to form a cycloalkyl group.

2. The composition of claim 1 where the hexahydropyrimidine contains at least 1 cycloalkylene group.

3. The composition of claim 2 where the cycloalkylene group of the hexahydropyrimidine is cyclohexyl.

4. The composition of claim 3 where the hexahydropyrimidine contains three cyclohexyl groups.

5. The composition of claim 2 where the hexahydropyrimidine has the formula

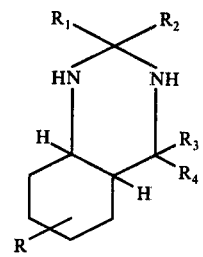

where the R's are hydrogen, alkyl, aryl, cycloalkyl, alkaryl, aralkyl, or heterocyclic.

6. The composition of claim 5 where the hexahydropyrimidine has the formula

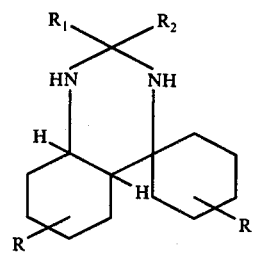

where the R's are hydrogen, alkyl, aryl, cycloalkyl, alkaryl, aralkyl, or heterocyclic.

7. The composition of claim 4 where the hexahydropyrimidine has the formula

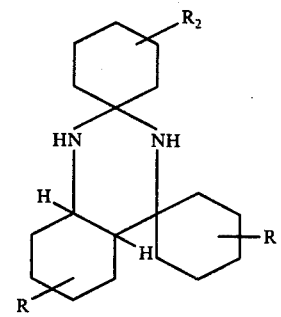

where the R's are hydrogen or alkyl.

8. The composition of claim 7 where the hexahydropyrimidine is 2,2,4,4-dipentamethylene-5,6-tetramethylene hexahydropyrimidine.

9. The composition of claim 7 which is non-staining.

10. The composition of claim 8 which is non-staining.

11. The composition of claim 1 where the rubber is natural rubber.

12. The composition of claim 1 where the rubber is a polymer of butadiene.

13. The composition of claim 1 where the rubber is a copolymer of butadiene and styrene.

14. The composition of claim 8 where the rubber is a copolymer of butadiene and styrene.

* * * * *